United States Patent [19]

Tachibana et al.

[11] Patent Number: 5,055,612

[45] Date of Patent: Oct. 8, 1991

[54] PROCESS FOR THE PREPARATION OF NAPHTHALENE CARBOXYLIC ACIDS

[75] Inventors: Yakudo Tachibana, Kasukabe; Kazuhiko Tate, Yokohama; Masami Ono, Yokohama; Nobuhiro Takei, Yokohama; Jun Miki, Yokohama; Hiroaki Taniguchi, Kuki; Yoshimi Shiroto, Yokohama; Misunori Shimura, Yokohama; Yoshio Fukui, Tokyo, all of Japan

[73] Assignees: NKK Corporation; Chiyoda Corporation, both of Japan

[21] Appl. No.: 451,952

[22] Filed: Dec. 19, 1989

[30] Foreign Application Priority Data

Dec. 19, 1988 [JP] Japan ................................. 63-320207
Dec. 19, 1988 [JP] Japan ................................. 63-320208
Dec. 19, 1988 [JP] Japan ................................. 63-320209
Dec. 19, 1988 [JP] Japan ................................. 63-320210

[51] Int. Cl.$^5$ ............................................. C07C 51/265
[52] U.S. Cl. .................................... 562/416; 562/417; 562/488
[58] Field of Search ..................... 562/416, 417, 488

[56] References Cited

U.S. PATENT DOCUMENTS 4,709,088 11/1987 Hirose et al. ..................... 562/414
4,716,245 12/1987 Hirose ............................. 562/416
4,754,060 6/1988 Hayashi et al. ................... 562/414

Primary Examiner—Jose G. Dees
Assistant Examiner—Vera C. Clarke
Attorney, Agent, or Firm—Lorusso & Loud

[57] ABSTRACT

A process for the preparation of naphthalene mono or polycarboxylic acids, such as 2,6-naphthalene dicarboxylic acid, is disclosed which includes oxidizing a naphthalene compound such as 2,6-diisopropylnaphthalene in a specific solvent with molecular oxygen in the presence of a catalyst containing a heavy metal compound and a bromine compound. The solvent is an aliphatic monocarboxylic acid and may further contain benzene and/or water. By controlling the ratio of the amount of catalyst metal to the feed rate of the raw material naphthalene compound, the yield of desired product can be controlled.

8 Claims, 2 Drawing Sheets

PROCESS FOR THE PREPARATION OF NAPHTHALENE CARBOXYLIC ACIDS

BACKGROUND OF THE INVENTION

The present invention relates to a process for the preparation of naphthalene carboxylic acids, in particular 2,6-naphthalene dicarboxylic acid.

2,6-naphthalene dicarboxylic acid is used as a starting material for synthesizing polyesters or polyamides useful as films or textile materials.

In the past, a number of improved processes for preparing naphthalenedicarboxylic acids (referred to hereinafter simply as NDC) have been proposed wherein diisopropylnaphthalene (referred to hereinafter simply as DiPN) is oxidized with molecular oxygen. The objects of the improvements are roughly classified as directed to one of two problems; instability of naphthalene nucleus in DiPN and the process of conversion of the isopropyl group into carboxyl group. The improvement in the former problem is directed to the instability of naphthalene nucleus itself. As the nucleus-substituted alkyl groups are not limited to an isopropyl group, the improved techniques utilize the alkyl-substituted naphthalenes. Typical improved techniques are the low temperature oxidation process as disclosed in Japanese Patent Publn. No. Sho. 48-27318, the two-step temperature elevation oxidizing process as disclosed in Japanese Patent Publn. No. Sho. 59-13495, and the oxidation process for a low concentration of the starting material as disclosed in Japanese Patent Publn. No. Sho. 56-3337. Even if these oxidation processes are utilized directly for the oxidation of DiPN, they are not effective for the preparation of NDC, so far as the latter problem residing in the conversion of isopropyl group is not solved.

A process employing a large amount of the catalyst has been proposed as represented by Japanese Laid-open Patent Appln. Nos. Sho. 60-89445, Sho. 60-89446 and Japanese Laid-open Patent Appln. No. Sho. 61-140540 which seems to be a collective edition of these references. This latter approach used the catalyst in an amount of about 10 times larger than in the conventional method and succeeded in increasing the yield of NDC on the assumption that when DiPN is oxidized under the conventional conditions for using a catalyst for oxidation of 2,6-dimethylnaphthalene, the catalyst will temporarily be deactivated and no side-reaction will take place because the isopropyl groups are abnormally rapid in the formation of an oxidation intermediate at the initial stage of the reaction as compared with the methyl groups. This process was indeed epoch-making as the oxidation process of DiPN and the yield of NDC was greatly increased.

For a process employing a large amount of the catalyst, which is said to be typical in the conventional techniques, various methods have been proposed; for example, there are proposed methods defining the amount of catalytic heavy metal per mol of DiPN or its oxidation intermediate (Japanese Laid-open Patent Appln. Nos. Sho. 60-89446 and 61-140540), Methods defining the amount of the starting material per gram catalytic heavy metal in case of a reaction mode wherein the starting material for oxidation is continuously or semicontinuously supplied to the reaction system (Japanese Laid-open Patent Appln. No. Sho. 61-140540), and methods defining the amount of DiPN and/or its oxidation intermediate per gram atom of the catalytic heavy metal in the oxidation reaction mixture (Japanese Laid-open Patent Appln. Nos. Sho. 60-89445 and 61-140540). However, these were all definitions for the amounts and did not address reaction rate.

The use of a process employing a large amount of the catalyst certainly increases the yield of NDC. However, it is a matter of course that a reaction other than a batchwise, for example, a semi-batchwise reaction wherein the starting material is continuously and/or semi-continuously supplied a continuous process wherein the starting material is continuously and/or semi-continuously supplied and the oxidation reaction mixture is continuously and/or semi-continuously taken out, necessitates consideration of rate of supply of the starting material Although known that the semi-batchwise or continuous reaction wherein the starting material is continuously and/or semi-continuously supplied is preferable to maintain the concentration of an oxidation intermediate at a lower level, a concrete means for controlling it has not previously been proposed.

In addition, it was practically impossible to control the amount of DiPN and/or an oxidation intermediate per gram of the catalytic heavy metal element in the oxidation reaction mixture during the pressure reaction. In short, the relation between the conditions in the reactor and the velocity of supply of the starting material capable of industrial application in the semi-batchwise or continuous reaction was not as yet clear for a process employing a large amount of the catalyst.

When the reaction is carried out in the semibatchwise mode, eventually when employing a large amount of the catalyst., there is a problem that only a result similar to the batchwise reaction is obtained if the rate for supplying the starting material is excessively great. Further, there is also a problem that producibility is reduced without perceiving that unnecessary large amount of the catalyst is used in proportion to the amount of the starting material treated.

One of the problems encountered in the preparation of NDC by oxidation with molecular oxygen is the ring-opening reaction of naphthalene which forms large amounts of phthalic acid derivatives and trimellitic acid (referred to hereinafter simply as TMA), thus causing insolubilization and deactivation of the catalytic heavy metals or coprecipitation of NDC with byproducts.

Roughly two alternative methods have been proposed to solve the foregoing problem. One of them comprises weakening the acidity of the oxidation reaction solvent to inhibit side-reactions and uses as the solvent propionic acid (Japanese Laid-open Patent Appln. No. Sho. 62-120342), butyric acid, valeric acid and benzoic acid (Japanese Laid-open Patent Appln. No. Sho. 62-120343). The other method takes into consideration the composition of the catalytic heavy metals and uses cobalt (Co)/nickel (Ni)/bromine (Br) catalyst (Japanese Laid-open Patent Appln. No. Sho. 62-212343) and cobalt (Co)/cerium (Ce)/bromine (Br) catalyst (Japanese Laid-open Patent Appln. No. Sho. 62-212344). In the method reducing the acidity of the solvent, side-reaction is inhibited to a certain degree but the solvent used is more expensive than acetic acid which is widely used. In addition, the stability to oxidation of the solvent per se is low and the combustion loss is great. In the method taking into consideration on the composition of catalyst, the oxidation power of the catalyst per se is eventually weakened so that the production rate of TMA is somewhat decreased but the yield of NDC is not increased. Thus, the NDC product is contaminated with intermediates and the cost of the catalyst is increased.

As the production of TMA as by-product is thus unavoidable, there is an idea of producing both NDC and TMA originally has been proposed (Japanese Laid-open Patent Appln. No. Sho. 62-212340).

In order to enhance the yield of NDC at a lower catalyst concentration, there is known a process wherein a mixture of an aliphatic carboxylic acid and chlorobenzene, bromobenzene or nitrobenzene is used as the reaction solvent (Japanese Laid-open Patent Appln. No. 62-255448). However, the benzene derivative used in this process is a strong solvent for the catalyst, the dissociation of DiPN and the catalyst is disturbed to make the yield of NDC dissatisfactory.

SUMMARY OF THE INVENTION

It is, therefore, an object of this invention to provide a process for preparing NDC wherein DiPN is oxidized by molecular oxygen in the presence of a catalyst of a heavy metal and a bromine compound, which process inhibiting side-reactions to increase the yield of NDC.

It is another object of the present invention to provide an advantageous process for carrying out the above process in a continuous or semi-continuous mode.

It is still another object of the present invention to provide a process for obtaining NDC in a high yield without any formation of trimellitic acid (TMA).

It is further object of the present invention to provide a process for obtaining NDC and TMA in a high total yield even if TMA is obtained as by-product.

It is still further object of the present invention to provide a process for preparing naphthoic acid and/or naphthalenedicarboxylic acid at a high yield from a starting material carrying a naphthalene nucleus.

As a result of extensive research made to attain the above objects, it has now been found that an increased yield of NDC can be achieved by continuously or semi-continuously supplying DiPN to a reactor for oxidation when DiPN is supplied to the reactor in such manner that the relation between the total amount of the catalytic heavy metal M (mol) and the rate of the DiPNF feed (mol/hour) satisfies $M/F \geq 2$, and that the ratio of NDC to TMA can be controlled by adjusting the M/F ratio.

It has also been found that the yield of NDC can be increased when an aliphatic monocarboxylic acid containing water in the amount of 15-55 mol% is used as the reaction solvent in the production of NDC from DiPN.

It has further been found that the yield of NDC can be increased by using a mixture of benzene and an aliphatic monocarboxylic acid as the reaction solvent in the production of NDC from DiPN, and that when this solvent is used, the starting material is not limited to DiPN but rather, any starting material carrying a naphthalene nucleus can be oxidized to the corresponding naphthalenecarboxylic acid in a good yield.

In accordance with the present invention, there is provided a process for the preparation of 2,6-naphthalene dicarboxylic acid which comprises oxidizing 2,6-diisopropylnaphthalene in a solvent containing an aliphatic monocarboxylic acid with molecular oxygen in the presence of a catalyst containing a heavy metal compound and a bromine compound wherein the oxidation is carried out by continuously and/or semi-continuously supplying the 2,6-diisopropylnaphthalene to a reactor in such manner that the relation between the total catalytic heavy metal M (mol) and the rate of the feed the 2,6-diisopropylnaphthalene F (mol/hour) to the reactor satisfies the equation $M/F \geq 2$.

In accordance with the present invention, there is also provided a process for the preparation of naphthoic acid and/or naphthalenepolycarboxylic acids which comprises oxidizing a starting material carrying a naphthalene nucleus in a solvent with molecular oxygen in the presence of a catalyst of a transition metal-bromine series, wherein a mixture of benzene and an aliphatic monocarboxylic acid is used as the solvent.

BRIEF DESCRIPTION OF THE DRAWINGS

Other objects, features and advantages of the invention will become apparent from the detailed description of the invention which follows, when considered in light of the accompanying drawings, in which.

DETAILED DESCRIPTION OF THE INVENTION

Figure 2:
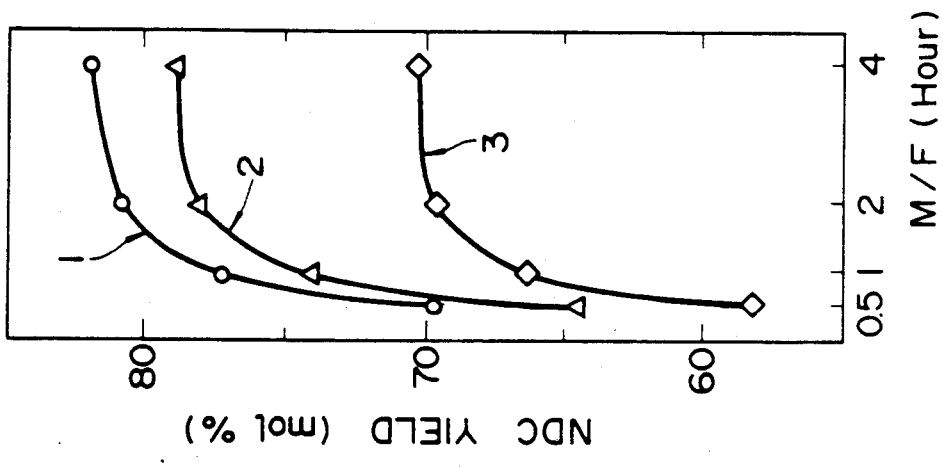
FIG. 2 is a graph showing results of the reactions of Example 2.

As the molecular oxygen used as the oxidizing agent in the present invention, pure oxygen or a mixture of pure oxygen and a diluting inert gas may be used, but in practice, air is most easily available and is a cheap gas containing molecular oxygen. These can be used directly or after being mixed with oxygen and/or other inert gas to adjust the oxygen concentration.

The catalysts of heavy metal-bromine series are known per se and are utilized industrially for the oxidation of alkylbenzenes. The heavy metal in this catalyst is in the form of a transition metal compound soluble in the reaction liquid. Preferably, one or more of cobalt, manganese, cerium and the like is used. Especially preferable is a combination of cobalt and manganese, and the range of the composition $Mn/(Mn+Co)$ (atomic ratio) is 0.2-0.9, preferably 0.5. As the bromine constituting the catalyst, any of the compound can be used so long as it supplies bromine ion in the reaction system. As coexistence of an alkali metal ion is effective for maintaining the state of ionization, it can be used in the form of a salt of bromine, for example, sodium bromide, potassium bromide, lithium bromide, etc. If the amount of bromine is excessively small, the rate of reaction will be low. On the other hand, if the amount is excessively large, the amount of by-products will be increased. Accordingly, the ratio of bromine/total catalytic heavy metal (atomic ratio) is preferably 0.01-1, more preferably 0.05-0.3. Accordingly, with the preferred combination of Co and Mn the preferred atomic ratio $Br/(Co+Mn)$ is 1/100 to 50:50. As described above, sodium, potassium, lithium and the like alkali metal ions are effective for maintaining the bromine in the state of ionization. As cocatalysts, therefore, these salts (bromine compounds) and/or a salt of an aliphatic monocarboxylic acid (the solvent) can be used. Its amount is preferably alkali metal/bromine (atomic ratio) $= 1-5$.

The reaction solvent of this invention is an aliphatic monocarboxylic acid. A lower aliphatic monocarboxylic acid having a carbon atom of at most 3 is preferable as the reaction solvent. Most suitable is acetic acid. This reaction solvent may contain water. The yield of NDC can be increased by controlling the amount of water in the solvent. One of the preferable reaction solvents used in the present invention is a mixture of an aliphatic monocarboxylic acid/water having a water content of 15-55 mol%, preferably 15-45 mol%, more preferably 15-30 mol%.

All of the water such as water formed during the reaction and water of crystallization in the catalyst is included in the aforementioned water content. In this invention, the ratio of mixing the aliphatic monocarboxylic acid and water at the initiation of the reaction is in the above mentioned range. It is inevitable that the water content will increase due to the water formed with the progress of the reaction or decrease due to the evaporation of water during the reaction. However, no particular limitation exists with regard to the water content after initiation of the reaction. A specific amount of water is allowed to exist in the reaction system at the initial stage of the reaction where abnormal reactions tend to occur, whereby the reaction is promoted stably to increase the yield of NDC. After the stage where abnormal reactions tend to occur is over, the water in the reaction solvent may adversely affect the completion of the reaction. Accordingly, the water content is preferably maintained at 30 mol% or less irrespective of the progress of the reaction. It is desirable to dehydrate the reaction system the 15 mol% at the completion of the reaction.

In the present invention it is preferable to use a mixture of benzene and an aliphatic monocarboxylic acid as the reaction solvent. While benzene is an excellent solvent for DiPN, it fails to dissolve the catalyst. However, when benzene is used in conjunction with an aliphatic monocarboxylic acid, NDC may be obtained with both a high yield and a high selectivity while suppressing the occurrence of side reactions. The benzene in the reaction mixture is considered to serve to facilitate association of oxygen (oxidizing agent) with the catalyst dissolved in the aliphatic monocarboxylic acid.

The use of benzene also permits reduction of the amount of the catalyst used and makes it easy to recover unreacted raw materials together with the solvent. That is, when the oxidation off gas emitted overhead from the reaction zone is fed to a condenser, the azeotropic mixture entrained by the oxidation off gas can be recovered as a condensate. The condensate is spontaneously separates into a lower, aqueous layer and an upper, benzene layer which contains the aliphatic monocarboxylic acid, DiPN and bromine compounds derived from the catalyst. Therefore, the benzene layer can be advantageously recycled to the reaction zone for the effective utilization of the unreacted raw material and the solvent. The use of benzene provides an additional advantage that DiPN in which is readily decomposed upon contact with a solution of the catalyst in an aliphatic monocarboxylic acid, can be fed to the reaction zone in a stable manner by dissolving same in benzene.

The content of benzene in the mixed solvent is generally 5-80 % by weight based on the total weight of the benzene and monocarboxylic acid. The proportion of benzene in the reaction mixture discharged from the reaction zone can, however, be outside of the above range since it depends upon the feed rates of the reactants and the amount of the reactants previously charged into the reaction zone. The mixture of benzene and an aliphatic monocarboxylic acid may further contain water in an amount of up to 15 %, more preferably up to 10 % based on the weight of the aliphatic monocarboxylic acid. This amount includes water formed in situ in the reaction zone and crystallization water contained in the catalyst.

The reaction temperature is preferably 160-200 °C., more preferably 170-190 °C. Too low a reaction temperature is undesirable because the reaction rate becomes slow and the productivity becomes poor. Too high a reaction temperature is also disadvantageous because the by-products are produced in an increased amount and the yield of NDC is lowered.

The reaction proceeds in a more accelerated manner as the partial pressure of oxygen increases. However, a desirable reaction rate is obtainable when the reaction pressure is controlled to provide a partial oxygen pressure of 0.2-8 kg/cm$^2$ (absolute pressure).

Since the oxidation of DiPN is a reaction which proceeds by gas/liquid contact, it is necessary to use a highly efficient reactor with which the gas/liquid contact does not represent a rate determining factor. Thus, the rate of discharge of the by-product gas from the reaction zone is important. For this reason, it is preferred that a gas containing molecular oxygen be fed to the reaction zone in an amount providing the following conditions: $G/L \geq 1$ (min$^{-1}$) wherein G represents the feed rate (normal liter/min) of the gas and L represents the amount (liter) of the reaction liquid.

After the completion of the reaction, NDC is separated and recovered from the reaction mixture and is purified in a manner known per se. The reaction mixture from which NDC has been separated may be subjected to a post treatment for the recovery of unreacted materials and the solvent in any known manner.

The reaction according to the present invention may be advantageously carried out in a continuous system or a semi-batch (semi-continuous) system. For this purpose, it is preferable to feed DiPN continuously or intermittently at a feed rate so that the ratio (M/F (hour)) of the total amount (M (mole)) of the catalyst, calculated as heavy metal, in the reactor to the feed rate (F (mole/hour)) of DiPN is maintained not lower than 2, i.e. $M/F \geq 2$.

In order to increase the M/F ratio, it is necessary to reduce the feed rate of NiNP per unit amount of the catalyst or to increase the amount of the catalyst per unit DiPN feed rate. Therefore, an increase of the M/F ratio has a great influence upon the productivity. An increase of the M/F ratio slightly increases the yield of NDC. Thus, the M/F ratio should be preferably selected in due consideration of the economy of ht process. Generally, the use of an M/F ratio in the range of 2-20 is recommendable.

The ratio NDC/TMA in the product may be controlled by control of the M/F ratio. Thus, the total yield of NDC and TMA can be increased by feeding DiPN at such a feed rate as to produce the M/F ratio in the range of 2-6. By this, the molar yield of NDC + TMA is maximum. In this case, however, it is necessary to purify NDC and to recover TMA and the catalyst heavy metals, since TMA and the heavy metals contaminate the crude NDC crystals. On the other hand, the yield of TMA can be decreased to substantially zero by feeding DiPN at such a feed rate as to provide the M/F ratio of 10 or more. In this case, inactivation of the catalyst can be prevented so that it becomes unnecessary to use equipment for recovering TMA and the catalyst heavy metals and for regenerating the catalyst. The crude NDC can be purified in a very simple manner.

When the process of the present invention is carried out in a semi-batch mode, the reactor is first charged with the solvent and the catalyst. Then, while introducing a molecular oxygen-containing a gas and while maintaining the temperature and the pressure in the reactor, DiPN is fed to the reactor continuously or intermittently so as to maintain a M/F ratio of at least 2. Thereafter, the feed of the oxygencontaining gas is continued until NDC is obtained in a desired amount.

When the process is carried out continuously, the raw material is fed continuously while continuously discharged the reaction produces in such a manner as to maintain the M/F ratio of at least 2.

For the purpose of preventing loss of the starting materials and the reaction intermediate from the reaction system and thereby improving the yield of NDC, it is preferred that a post reactor be provided downstream of a main reactor to which DiPN is fed. The post reactor is of a type in which gas/liquid contact is effected one or more times. The reaction conditions (temperature, pressure, etc.) in the post reactor are preferably the same as those in the main reactor, though different conditions may be used, if desired. When such a post reactor is used, M of the above-specified M/F ratio refers to the total amount of the catalyst (as heavy metals) in the main reactor.

Since DiPN has a melting point of about 70 °C and is solid at room temperature, it is necessary to feed DiPN to the reactor in a melted state with heating. Alternatively, DiPN may be fed in the form of a solution in a solvent which is inert to the aliphatic monocarboxylic acid and does not adversely affect the desired reaction. However, it is advisable not to use a catalyst-containing solvent such as a mother liquor recovered from the reaction mixture, since DiPN tends to deteriorate in the presence of the catalyst at an elevated temperature with the simultaneous inactivation of the catalyst.

As described above, control of the M/F ratio at 2 or more involves control a the amount of the catalyst heavy metals so as to allow a DiPN feed rate suitable for avoiding inactivation of the catalyst. By this, the reaction can be continuously performed while maintaining suitable catalytic activity. As a result, the occurrence of side reactions can be suppressed, enabling production of NDC with a high yield and with a high selectivity. Additionally, the productivity or process efficiency can be improved because it is possible to determine the minimum amount of the catalyst required for obtaining optimum results from the feed rate of DiPN.

The various above merits deriving from the use of a mixture containing benzene and an aliphatic monocarboxylic acid as the reaction solvent are also equally obtainable when such a mixed solvent system is used for oxidation of naphthalene compounds other than DiPN by molecular oxygen in the presence of a catalyst composed of a heavy metal compound and a bromine compound. Such naphthalene compounds include monoalkylnaphthalenes, polyalkylnaphthalenes, alkylacylnaphthalenes, acenaphthenes and acylacenaphthenes. These raw materials give corresponding naphthalene monocarboxylic acids (naphthoic acid) or polycarboxylic acids. These raw materials may contain one or more inert substituents such as alkoxy, nitro and halogen. The oxidation can be performed in a batch, semi-batch or continuous mode. The reaction temperature may vary with the kind of the raw material but is generally in the range of 80–210 °C.

The present invention will now be illustrated in more detail by way of examples and comparative examples.

EXAMPLE 1

Using a titanium-lining pressure reactor equipped with a reflux condenser, a gas-inlet and -outlet, a continuous feed-supplying pump and a stirrer, an oxidation reaction was carried out at levels as shown in Table 1. In this case, the feed rate of of DiPN was held constant, while the M/F ratio was varied by the amount of catalyst used.

The reactor was charged with acetic acid and catalysts in amounts as shown in Table 1. Under agitation (NK type atomizer, stirring peripheral velocity 7 m/sec), pure oxygen was blown into the reactor $[G/L=2\ (min^{-1})]$ and the temperature and the oxygen pressure were adjusted to 170° C. and 8 kg/cm$^2$ (absolute pressure), respectively. DiPN was then continuously supplied for 2 hours at a feed rate of $7.5 \times 10^{-2}$(mol/hour) and the pure oxygen was continuously blown into the reactor for 2 hours.

Figure 1:
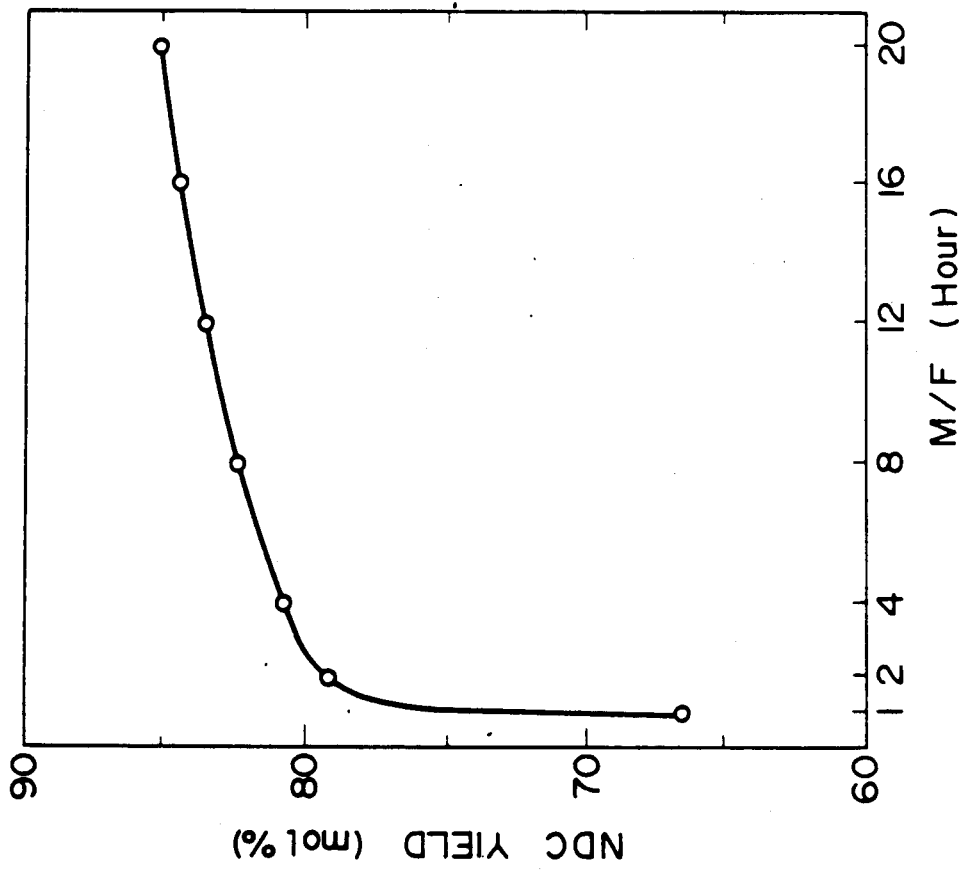
FIG. 1 is a graph showing results of the reactions of Example 1.

After completion of the reaction, the reactor was cooled and released from the pressurization and the reaction liquid was taken out from the reactor and subjected to solidliquid separation. The product thus obtained was subjected to liquid chromatography to check the yield of NDC. The results of the reaction are shown in FIG. 1.

TABLE 1

| Exp. No. | Acetic acid | Amount used (mol) | | | | Amount of DiPN totally supplied (mol) | M/F (hour) |
| --- | --- | --- | --- | --- | --- | --- | --- |
| | | Manganese acetate tetrahydrate | Cobalt acetate tetrahydrate | Sodium Bromide | Sodium acetate trihydrate | | |
| 1 | 15 | $3.75 \times 10^{-2}$ | $3.75 \times 10^{-2}$ | $1.25 \times 10^{-2}$ | $3.75 \times 10^{-2}$ | $1.5 \times 10^{-1}$ | 1 |
| 2 | " | $7.5 \times 10^{-2}$ | $7.5 \times 10^{-2}$ | $2.5 \times 10^{-2}$ | $7.5 \times 10^{-2}$ | " | 2 |
| 3 | " | $1.5 \times 10^{-1}$ | $1.5 \times 10^{-1}$ | $5 \times 10^{-2}$ | $1.5 \times 10^{-1}$ | " | 4 |
| 4 | " | $3 \times 10^{-1}$ | $3 \times 10^{-1}$ | $1 \times 10^{-1}$ | $3 \times 10^{-1}$ | " | 8 |
| 5 | " | $4.5 \times 10^{-1}$ | $4.5 \times 10^{-1}$ | $1.5 \times 10^{-1}$ | $4.5 \times 10^{-1}$ | " | 12 |
| 6 | " | $6 \times 10^{-1}$ | $6 \times 10^{-1}$ | $2 \times 10^{-1}$ | $6 \times 10^{-1}$ | " | 16 |
| 7 | " | $7.5 \times 10^{-1}$ | $7.5 \times 10^{-1}$ | $2.5 \times 10^{-1}$ | $7.5 \times 10^{-1}$ | " | 20 |

Note: Catalyst condition: Mn/(Mn + Co) = 0.5, Br/(Mn + Co) = 1/6, Na/Br = 4

EXAMPLE 2

Using a pressure reactor of a 1/1C scale similar to that used in Example 1, an oxidation reaction was carried out at levels as shown in Table 2. In this case, the amounts of catalysts used and the feed rate were adjusted to vary the M/F ratio. In this Example 2, the experiments were carried out under the same reaction conditions as described in Example 1 except that the feed rate of DiPN was adjusted to different experimental levels and the atomizer diameter was ½ of that used in Example 1 so that the stirring peripheral velocity of the NK type atomizer was 3.5 m/sec. The results of the experiments are shown in FIG. 2.

TABLE 2

| Exp. No. | Amount used (mol) | | | | Amount of DiPN totally supplied* (mol) | M/F (hour) |
|---|---|---|---|---|---|---|
| | Acetic acid | Manganese acetate tetrahydrate | Cobalt acetate tetrahydrate | Sodium Bromide | Sodium acetate trihydrate | | |
| 8 | 1.5 | $3.75 \times 10^{-3}$ | $3.75 \times 10^{-3}$ | $1.25 \times 10^{-3}$ | $3.75 \times 10^{-3}$ | $3 \times 10^{-2}$ | 0.5 |
| 9 | " | " | " | " | " | $1.5 \times 10^{-2}$ | 1 |
| 10 | " | " | " | " | " | $7.5 \times 10^{-3}$ | 2 |
| 11 | " | " | " | " | " | $3.75 \times 10^{-3}$ | 4 |
| 12 | " | $7.5 \times 10^{-3}$ | $7.5 \times 10^{-3}$ | $2.5 \times 10^{-3}$ | $7.5 \times 10^{-3}$ | $6 \times 10^{-2}$ | 0.5 |
| 13 | " | " | " | " | " | $3 \times 10^{-2}$ | 1 |
| 14 | " | " | " | " | " | $1.5 \times 10^{-2}$ | 2 |
| 15 | " | " | " | " | " | $7.5 \times 10^{-3}$ | 4 |
| 16 | " | $1.5 \times 10^{-2}$ | $1.5 \times 10^{-2}$ | $5 \times 10^{-3}$ | $1.5 \times 10^{-2}$ | $1.2 \times 10^{-1}$ | 0.5 |
| 17 | " | " | " | " | " | $6 \times 10^{-2}$ | 1 |
| 18 | " | " | " | " | " | $3 \times 10^{-2}$ | 2 |
| 19 | " | " | " | " | " | $1.5 \times 10^{-2}$ | 4 |

*Continuously supplied time = 2 hours

EXAMPLE 3

Using a titanium-lined pressure reactor equipped with a reflux condenser, a gas-inlet and -outlet, a continuous feed-supplying pump and a stirrer, an oxidation reaction was carried out at levels as shown in Table 3. In this case, the feed rate of DiPN was held constant, while the M/F ratio was varied in by the amounts of catalysts used.

Figure 3:
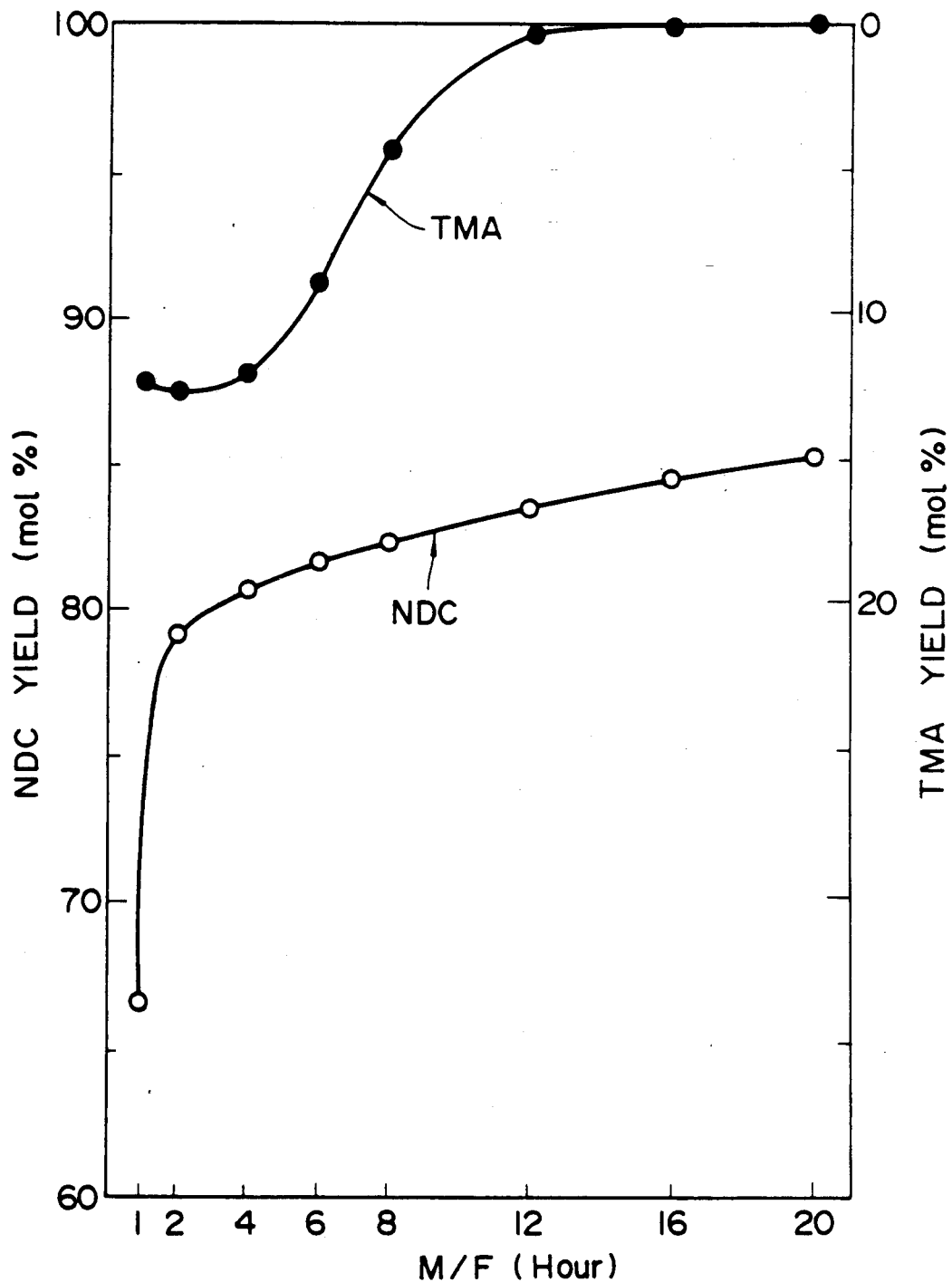
FIG. 3 is a graph showing results of the reactions of Example 3.

The reactor was charged with acetic acid and catalysts in amounts as shown in Table 1. Under agitation (NK type atomizer, stirring peripheral velocity 7 m/sec), pure oxygen was blown into the reactor [G/L=2 (min$^{-1}$)] and the temperature and the oxygen pressure were adjusted to 170° C. and 8 kg/cm$^2$ (absolute pressure), respectively. DiPN was then continuously supplied for 2 hours at a feed rate of $7.5 \times 10^{-2}$ (mol/hour) and the pure oxygen was continuously blown into the reactor for 2 hours. After completion of the reaction, the reactor was cooled and released from the pressurization and the reaction liquid was taken out from the reactor and subjected to solid-liquid separation. The product thus obtained was subjected to liquid chromatography to check the yields of NDC and TMA. The results of the reaction are shown in FIG. 3.

TABLE 3

| Exp. No. | Amount used (mol) | | | | | M/F (hour) |
|---|---|---|---|---|---|---|
| | Acetic acid | Manganese acetate tetrahydrate | Cobalt acetate tetrahydrate | Sodium Bromide | Sodium acetate trihydrate | |
| 1 | 15 | $3.75 \times 10^{-2}$ | $3.75 \times 10^{-2}$ | $1.25 \times 10^{-2}$ | $3.75 \times 10^{-2}$ | 1 |
| 2 | " | $7.5 \times 10^{-2}$ | $7.5 \times 10^{-2}$ | $2.5 \times 10^{-2}$ | $7.5 \times 10^{-2}$ | 2 |
| 3 | " | $1.5 \times 10^{-1}$ | $1.5 \times 10^{-1}$ | $5 \times 10^{-2}$ | $1.5 \times 10^{-1}$ | 4 |
| 4 | " | $2.25 \times 10^{-1}$ | $2.25 \times 10^{-1}$ | $7.5 \times 10^{-2}$ | $2.25 \times 10^{-1}$ | 6 |
| 5 | " | $3 \times 10^{-1}$ | $3 \times 10^{-1}$ | $1 \times 10^{-1}$ | $3 \times 10^{-1}$ | 8 |
| 6 | " | $4.5 \times 10^{-1}$ | $4.5 \times 10^{-1}$ | $1.5 \times 10^{-1}$ | $4.5 \times 10^{-1}$ | 12 |
| 7 | " | $6 \times 10^{-1}$ | $6 \times 10^{-1}$ | $2 \times 10^{-1}$ | $6 \times 10^{-1}$ | 16 |
| 8 | " | $7.5 \times 10^{-1}$ | $7.5 \times 10^{-1}$ | $2.5 \times 10^{-1}$ | $7.5 \times 10^{-1}$ | 20 |

Note: Catalyst composition: Mn/Co = 50/50, Br/(Mn + Co) = 1/6, Na/Br = 4

As is evident from the results shown in FIG. 3, it is now possible to control the amount of TMA by-produced while keeping the yield of NDC higher by using an industrially practical control factor M/F according to the present invention. Thus, either enhancement of the rate of utilization of DiPN (byproduction of TMA) or production of a high purity NDC (without TMA) can be chosen. In addition, the reaction solvents and the catalysts used in the present invention are widely used in industrial fields so that there is no factor of increased cost.

COMPARATIVE EXAMPLE 1

A titanium-lined pressure reactor equipped with a reflux condenser, a gas-inlet and -outlet and a stirrer was charged with the following ingredients:

| | |
|---|---|
| DiPN | $2.36 \times 10^{-2}$ mol |
| Acetic acid [CH$_3$COOH] | 2.25 mol |
| Cobalt acetate tetraacetate [Co(OCOCH$_3$)$_2$ 4H$_2$O] | $2.36 \times 10^{-2}$ mol |
| Manganese acetate tetrahydrate [Mn(OCOCH$_3$)$_2$ 4H$_2$O] | $2.36 \times 10^{-2}$ mol |
| Sodium bromide (NaBr) | $7.87 \times 10^{-3}$ mol |
| Sodium acetate trihydrate [NaOCOCH$_3$ 3H$_2$O] | $2.36 \times 10^{-2}$ mol |

Into the starting mixture under pressure of 6 kg/cm$^2$ (absolute pressure) was introduced pure oxygen at G/L =2 min$^{-1}$. The mixture was vigorously stirred with an NK-type atomizer and heated rapidly up to 170 °C, and the reaction was carried out for 4 hours while maintaining this temperature.

Separately, a similar starting liquid was prepared and the water content was measured at 11.18 mol% based on the total amount of water and acetic acid. After the reaction the yield of NDC in the reaction mixture was determined to be 52.5 mol%.

EXAMPLE 4

An oxidation reaction of DiPN was carried out with the same starting materials and under the same conditions as Comparative Example 1 except that 0.4 mol of pure water was added to the same reactor as described in Comparative Example 1.

Separately, a similar starting liquid was prepared and the water content was measured to determine that the water content was 23.50 mol% based on the total amount of water and acetic acid.

After the reaction, the yield of NDC in the reaction mixture was determined to be 70.1 mol%.

EXAMPLE 5

An oxidation reaction was carried out under the same reaction conditions and with the same starting materials as described in Comparative Example 1 except that 1.4 mol of pure water was added and the amount of acetic acid used was 1.83 mol.

Separately, a similar starting liquid was prepared and the water content was measured at 47.76 mol% based on the total amount of water and acetic acid. After the reaction the yield of NDC in the reaction mixture was determined to be 63.4 mol%.

As is evident from the above Comparative Example 1 and Examples 4 and 5, a rapid reaction is inhibited and the amount of by-products is decreased even if a large amount of DiPN exists in the reaction liquid. As compared with the conventional method, the yield of NDC is increased under the same conditions and the amount of DiPN consumed is increased in the same reaction scale.

EXAMPLE 6-24 AND COMPARATIVE EXAMPLES 2-15

Using a titanium-lined pressure reactor equipped with a reflux condenser, a gas-inlet and -outlet, a continuous feed-supplying pump (using in case of semi-batchwise reaction) and a stirrer, oxidation of each starting material was carried out under the conditions as shown in Table 4. Used as the starting materials were 1-methylnaphthalene (1-MN), 2-methylnaphthalene (2-MN), 2-isopropylnaphthalene (2-iPN), 2,3-dimethylnaphthalene (2,3-DMN), 2,6-dimethylnaphthalene (2,6-DMN), 2,6-diisopropylnaphthalene (2,6-DiPN), acenaphthenen (An), 2-methyl-6-acetylnaphthalene (2-M-6-AcN) and 5-acetylacenaphthene (5-AcAn). Each starting material was highly pure grade of 99% or more.

The oxidizing liquid was prepared in accordance with different each experimental levels from acetic acid (AcOH), benzene ($C_6H_6$), cobalt acetate tetrahydrate (Co), manganese acetate tetrahydrate (Mn), ammonium bromide (Br) and sodium acetate trihydrate (Na).

Air, in which the oxygen content had been varied, pure oxygen, etc. was used as the oxidizing gas and the total pressure was adjusted to a given oxygen partial pressure.

In a batchwise reaction, the reactor was charged with a given amount of each ingredient and an oxidation reaction was carried out under each set of reaction conditions by blowing the oxidizing gas at a gas/liquid ratio $G/L=2(1/min)$ based on $O_2$.

In a semi-batchwise reaction, the reactor was charged with given amounts of the ingredients other than the starting material. Under given temperature and pressure conditions, the oxidizing gas was blown into the reactor at a gas/liquid ratio $G/L=2(1/min)$. Into the reactor in this state was pumped the starting material (a starting material which was solid at normal temperature but melted by heating). After continuously feeding the starting material in a given amount at a constant rate, the oxidizing gas was continuously blown for a given period of time.

After completion of the reaction, the reactor was cooled and released from pressurization in both of the batchwise and the semi-batchwise reaction and the reaction liquid was taken out. The reaction liquid was separated from any solid material and subjected to liquid chromatography to check the yield of each product. The amount of the ingredients used in the experiment and the results of the experiments are shown in Table 4 wherein "E" and "CE" stand for Example and Comparative Example, respectively.

These examples certify that the results obtained in Examples 6–19 were not a mere dilution effect of benzene. Examples 6–19 are different from Comparative Examples 2–15 in the starting materials and in the concentrations of catalysts. However, the amount of acetic acid used was decreased in Examples 20–24 so that the concentration might not be changed. The effect of the addition of benzene was taken into consideration in making the starting materials and the concentrations of catalysts identical for Comparative Examples 2, 8, 11, 13, and 15. Comparing Examples 6, 12, 15, 17 and 19 with Examples 20–24, the oxidation reaction is more or less influenced by the solvent composition, starting materials and the concentrations of the catalysts but the effect of the addition of benzene is not denied.

As is evident from Examples 20–24, the use of mixed solvents of benzene and an aliphatic monocarboxlic acid promotes the main reaction and inhibits the side reactions in the production of naphthoic acids and/or naphthalene polycarboxylic acids by oxidation of a starting material carrying a naphthalene nucleus with molecular oxygen in the presence of a catalyst. Thus, a highly pure product can be obtained in a high yield. In addition, there is a subsidiary effect in that the amount of the catalyst used can be reduced.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

TABLE 4

| No. | Starting material | reaction mode | Amount used (mol)* | | | | | | |
|---|---|---|---|---|---|---|---|---|---|
| | | | Starting material | AcOH | $C_6H_6$ | Co | Mn | Br | Na |
| E6 | 1-MN | batchwise | $1.0 \times 10^{-1}$ | 1.5 | 0.5 | $1.5 \times 10^{-3}$ | $3.0 \times 10^{-3}$ | $4.5 \times 10^{-3}$ | — |
| CE2 | | | | | — | | | | |
| E7 | 2-MN | batchwise | $2.0 \times 10^{-2}$ | 1.5 | 0.5 | $3.0 \times 10^{-3}$ | $9.0 \times 10^{-5}$ | $3.0 \times 10^{-3}$ | — |
| CE3 | | | | | — | | | | |
| E8 | 2-iPN | batchwise | $1.0 \times 10^{-2}$ | 1.5 | 0.5 | $5.0 \times 10^{-3}$ | $1.0 \times 10^{-2}$ | $2.5 \times 10^{-3}$ | — |
| CE4 | | | | | — | | | | |
| E9 | 2,3-DMN | batchwise | $3.0 \times 10^{-2}$ | 1.5 | 0.5 | $1.2 \times 10^{-3}$ | $1.2 \times 10^{-3}$ | $1.5 \times 10^{-3}$ | — |
| CE5 | | | | | — | | | | |
| E10 | 2,6-DMN | batchwise | $3.0 \times 10^{-2}$ | 1.5 | 0.5 | $1.2 \times 10^{-3}$ | $1.2 \times 10^{-3}$ | $1.5 \times 10^{-3}$ | — |

TABLE 4-continued

| No. | | | | | | | | | |
|---|---|---|---|---|---|---|---|---|---|
| CE6 | | | — | | | | | | |
| E11 | 2,6-DMN | semi-batchwise | $3.0 \times 10^{-2}$ | 1.5 | 0.5 | $1.2 \times 10^{-3}$ | $1.2 \times 10^{-3}$ | $1.5 \times 10^{-3}$ | — |
| CE7 | | | — | | | | | | |
| E12 | 2,6-DiPN | batchwise | $1.0 \times 10^{-2}$ | 1.5 | 0.5 | $1.0 \times 10^{-2}$ | $2.0 \times 10^{-2}$ | $5.0 \times 10^{-3}$ | — |
| CE8 | | | — | | | | | | |
| E13 | 2,6-DiPN | semi-batchwise | $1.0 \times 10^{-2}$ | 1.5 | 0.5 | $1.0 \times 10^{-2}$ | $2.0 \times 10^{-2}$ | $5.0 \times 10^{-3}$ | — |
| CE9 | | | — | | | | | | |
| E14 | An | batchwise | $3.0 \times 10^{-3}$ | 1.5 | 0.5 | $4.8 \times 10^{-4}$ | $9.6 \times 10^{-4}$ | $1.2 \times 10^{-3}$ | — |
| CE10 | | | — | | | | | | |
| E15 | An | semi-batchwise | $1.2 \times 10^{-2}$ | 1.5 | 0.5 | $4.8 \times 10^{-4}$ | $9.6 \times 10^{-4}$ | $1.2 \times 10^{-3}$ | — |
| CE11 | | | — | | | | | | |
| E16 | 2-M-6-AcN | batchwise | $1.0 \times 10^{-1}$ | 1.5 | 0.5 | — | $1.0 \times 10^{-2}$ | — | — |
| CE12 | | | — | | | | | | |
| E17 | 2-M-6-AcN | semi-batchwise | $1.0 \times 10^{-1}$ | 1.5 | 0.5 | $3.0 \times 10^{-3}$ | $3.0 \times 10^{-3}$ | $3.0 \times 10^{-3}$ | $3.0 \times 10^{-3}$ |
| CE13 | | | — | | | | | | |
| E18 | 5-AcAn | batchwise | $2.0 \times 10^{-2}$ | 1.5 | 0.5 | $3.0 \times 10^{-2}$ | $3.0 \times 10^{-2}$ | $1.0 \times 10^{-2}$ | $4.0 \times 10^{-2}$ |
| CE14 | | | — | | | | | | |
| E19 | 5-AcAn | semi-batchwise | $2.0 \times 10^{-2}$ | 1.5 | 0.5 | $3.0 \times 10^{-2}$ | $3.0 \times 10^{-2}$ | $1.0 \times 10^{-2}$ | $4.0 \times 10^{-2}$ |
| CE15 | | | — | | | | | | |
| E20 | 1-MN | batchwise | $1.0 \times 10^{-1}$ | 1.0 | 0.5 | $1.5 \times 10^{-3}$ | $3.0 \times 10^{-3}$ | $4.5 \times 10^{-3}$ | — |
| E21 | 2,6-DiPN | batchwise | $1.0 \times 10^{-2}$ | 1.0 | 0.5 | $1.0 \times 10^{-2}$ | $2.0 \times 10^{-2}$ | $5.0 \times 10^{-3}$ | — |
| E22 | An | semi-batchwise | $1.2 \times 10^{-2}$ | 1.0 | 0.5 | $4.8 \times 10^{-4}$ | $9.6 \times 10^{-4}$ | $1.2 \times 10^{-3}$ | — |
| E23 | 2-M-6-AcN | semi-batchwise | $1.0 \times 10^{-1}$ | 1.0 | 0.5 | $3.0 \times 10^{-3}$ | $3.0 \times 10^{-3}$ | $3.0 \times 10^{-3}$ | $3.0 \times 10^{-3}$ |
| E24 | 5-AcAn | semi-batchwise | $2.0 \times 10^{-2}$ | 1.0 | 0.5 | $3.0 \times 10^{-2}$ | $3.0 \times 10^{-2}$ | $1.0 \times 10^{-2}$ | $4.0 \times 10^{-2}$ |

| No. | Reaction condition** | | | Product | (mol %) |
|---|---|---|---|---|---|
| | Temp. (°C.) | O₂ pressure (kg/cm²) | time (h) | | |
| E6 | 115 | 2.0 | 1.0 | 1-Naphthoic acid | 82.0 |
| CE2 | | | | | 74.1 |
| E7 | 110 | 2.0 | 1.0 | 2-Naphthoic acid | 85.9 |
| CE3 | | | | | 80.2 |
| E8 | 160 | 6.0 | 3.0 | 2-Naphthoic acid | 88.7 |
| CE4 | | | | | 83.0 |
| E9 | 120 | 2.0 | 3.5 | Naphthalene 2,3-dicarboxylic acid | 72.3 |
| CE5 | | | | | 61.8 |
| E10 | 180 | 6.0 | 2.5 | Naphthalene 2,6-dicarboxylic acid | 77.4 |
| CE6 | | | | | 63.4 |
| E11 | 180 | 6.0 | 2 + 0.5 | Naphthalene 2,6-dicarboxylic acid | 83.5 |
| CE7 | | | | | 74.8 |
| E12 | 160 | 5.0 | 3.0 | Naphthalene 2,6-dicarboxylic acid | 71.3 |
| CE8 | | | | | 58.7 |
| E13 | 160 | 5.0 | 1 + 2.0 | Naphthalene 2,6-dicarboxylic acid | 82.8 |
| CE9 | | | | | 72.9 |
| E14 | 180 | 4.0 | 1.0 | Naphthalene 1,8-dicarboxylic acid | 72.0 |
| CE10 | | | | | 59.6 |
| E15 | 180 | 4.0 | 2 + 1.0 | Naphthalene 1,8-dicarboxylic acid | 81.9 |
| CE11 | | | | | 75.4 |
| E16 | 140 | 5.0 | 2.0 | Naphthalene 2,6-dicarboxylic acid | 75.6 |
| CE12 | | | | | 60.1 |
| E17 | 180 | 4.0 | 1 + 1.0 | Naphthalene 2,6-dicarboxylic acid | 85.2 |
| CE13 | | | | | 79.5 |
| E18 | 170 | 8.0 | 4.0 | Naphthalene 1,4,5-tricarboxylic acid | 69.1 |
| CE14 | | | | | 55.8 |
| E19 | 170 | 8.0 | 2 + 2.0 | Naphthalene 1,4,5-tricarboxylic acid | 78.2 |
| CE15 | | | | | 71.5 |
| E20 | 115 | 2.0 | 1.0 | 1-Naphthoic acid | 80.8 |
| E21 | 160 | 5.0 | 3.0 | Naphthalene 2,6-dicarboxylic acid | 71.6 |
| E22 | 180 | 4.0 | 2 + 1.0 | Naphthalene 1,8-dicarboxylic acid | 80.3 |
| E23 | 180 | 4.0 | 1 +1.0 | Naphthalene 2,6-dicarboxylic acid | 87.3 |
| E24 | 170 | 8.0 | 2 + 2.0 | Naphthalene 1,4,5-tricarboxylic acid | 81.7 |

Note:
*Where the reaction mode was semi-batchwise, the reactor was charged with the ingredients other than the starting material. After initiation of the reaction the starting material as shown was continuously fed for a given time.
**(1) O₂ pressure is absolute pressure. (2) Reaction time A + B in case of semi-batchwise reaction: A (time for supplying the starting material) B (time after supplying the starting material)

What is claimed is:

1. A process for the preparation of 2,6-naphthalene dicarboxylic acid which comprises oxidizing 2,6-diisopropylnaphthalene in a solvent containing an aliphatic monocarboxylic acid with molecular oxygen in the presence of a catalyst comprising a heavy metal compound and a bromine compound at a temperature of 160-200° C. and with an oxygen partial pressure of 0.2-8 kg/cm² absolute, and wherein the oxidation is carried out by continuously and/or semi-continuously supplying the 2,6-diisopropylnaphthalene to a reactor in such manner that the relation between the total catalytic heavy metal amount M (mol) and the feed rate F (mol/hour) of the 2,6-diisopropylnaphthalene satisfies the equation $M/F \geq 2$.

2. A process as claimed in claim 1, wherein said heavy metal compound is a mixture of a cobalt compound and a manganese compound and is contained in an amount providing a Co/Mn atomic ratio of 80:20 to 10:90 and a Br/(Co +Mn) atomic ratio of 1/100 to 50:50.

3. A process as claimed in claim 1, wherein the M/F ratio is controlled in the range of 2 to 6 so that the total yield of 2,6-naphthalene dicarboxylic acid and trimellitic acid is rendered maximum.

4. A process as claimed in claim 1, wherein the M/F ratio is controlled in the range of 10 or more so that the yield of 2,6-naphthalene dicarboxylic acid is rendered maximum.

5. A process as claimed in claim 1, wherein said aliphatic monocarboxylic acid-containing solvent has a water content of 15-55 mol %.

6. A process as claimed in claim 1, wherein said aliphatic monocarboxylic acid-containing solvent further contains benzene.

7. A process as claimed in claim 6, wherein said solvent has a benzene content of 5-80% by weight.

8. A process for the preparation of naphthalene monocarboxylic acid or polycarboxylic acid, which comprises oxidizing a naphthalene compound in a solvent with molecular oxygen in the presence of a catalyst comprising a heavy metal compound and a bromine compound at a temperature of 160-200° C. and with an oxygen partial pressure of 0.2-8 kg/cm$^2$ absolute, wherein said solvent is a mixture containing benzene and an aliphatic monocarboxylic acid and wherein said naphthalene compound is selected from the group consisting of monoalkylnaphthalenes, polyalkylnaphthalenes, alkylacylnaphthalenes, acenaphthenes and acylacenaphthenes.

* * * * *

UNITED STATES PATENT AND TRADEMARK OFFICE
CERTIFICATE OF CORRECTION

PATENT NO. : 5,055,612
DATED : October 8, 1991
INVENTOR(S) : Tachibana et al

Page 1 of 3

It is certified that error appears in the above-indentified patent and that said Letters Patent is hereby corrected as shown below:

Col. 1, line 24, delete "the" insert --other--;

line 52, delete "process";

line 60, delete "Methods" insert --methods--;

line 61, after "gram" insert --of the--.

Col. 2, line 6, delete "a", third instance;

line 7, after "wise," delete the period ".";

line 9, after "supplied" insert --or--;

line 14, after "material" insert a period --.--;

line 62, delete "to" and insert --against--;

line 64, delete "on".

Col. 3, line 4, delete "there is an";

line 22, delete "inhibiting" insert --inhibits--;

line 42, after "rate" insert --F--;

line 56, after "but" insert a comma --,--;

UNITED STATES PATENT AND TRADEMARK OFFICE
CERTIFICATE OF CORRECTION

PATENT NO. : 5,055,612

DATED : October 8, 1991

INVENTOR(S) : TACHIBANA et al

It is certified that error appears in the above-identified patent and that said Letters Patent is hereby corrected as shown below:

line 65, after "compound", second instance, insert a comma --,--.

Col. 4, line 2, after "feed" insert --of--;

line 43, delete "of the".

line 45, delete "is";

line 53, after "advantage" insert --in-- and after "DiPN" insert a comma --,--.

Col. 6, line 49, delete "ht" insert --the--;

line 57, delete "maximum" and insert --maximized--.

Col. 7, line 4, delete "a";

line 12, delete "charged" insert --charging--;

UNITED STATES PATENT AND TRADEMARK OFFICE
CERTIFICATE OF CORRECTION

PATENT NO. : 5,055,612

DATED : October 8, 1991

INVENTOR(S) : TACHIBANA et al

It is certified that error appears in the above-identified patent and that said Letters Patent is hereby corrected as shown below:

line 13, delete "the" and insert --a--.

Col. 8, line 22, delete "of", second instance;

line 38, delete "solidliquid" insert --solid liquid--.

Col. 11, line 27, "EXAMPLE" should read --EXAMPLES--.

Signed and Sealed this

Thirty-first Day of August, 1993

Attest:

BRUCE LEHMAN

*Attesting Officer*      *Commissioner of Patents and Trademarks*